(12) United States Patent
Kapadia et al.

(10) Patent No.: US 10,223,070 B2
(45) Date of Patent: *Mar. 5, 2019

(54) PRESORTER HOLDING SYSTEM AND METHOD FOR AUTOMATED PRESCRIPTION FULFILLMENT

(71) Applicant: Humana Inc., Louisville, KY (US)

(72) Inventors: Atin Kapadia, Chandler, AZ (US); Michael Mahar, Phoenix, AZ (US); Anu Payyapilly, Chandler, AZ (US); Andrew Bihnam, Scottsdale, AZ (US)

(73) Assignee: Humana Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/689,552

(22) Filed: Aug. 29, 2017

(65) Prior Publication Data

US 2018/0285075 A1 Oct. 4, 2018

Related U.S. Application Data

(63) Continuation of application No. 15/473,135, filed on Mar. 29, 2017, now Pat. No. 9,846,566.

(51) Int. Cl.
| | |
|---|---|
| *B65G 47/69* | (2006.01) |
| *G06F 7/06* | (2006.01) |
| *G06F 7/08* | (2006.01) |
| *B65G 43/08* | (2006.01) |
| *B65G 1/137* | (2006.01) |
| *G07F 17/00* | (2006.01) |
| *G06F 19/00* | (2018.01) |
| *B65G 47/82* | (2006.01) |

(52) U.S. Cl.
CPC ............. *G06F 7/08* (2013.01); *B65G 1/1373* (2013.01); *B65G 1/1378* (2013.01); *B65G 43/08* (2013.01); *B65G 47/69* (2013.01); *B65G 47/82* (2013.01); *G06F 7/06* (2013.01); *G06F 19/00* (2013.01); *G06F 19/3462* (2013.01); *G07F 17/0092* (2013.01); *B65G 2201/0261* (2013.01); *B65G 2203/0216* (2013.01); *B65G 2203/0233* (2013.01); *B65G 2203/044* (2013.01); *B65G 2203/046* (2013.01); *Y10T 156/1744* (2015.01); *Y10T 156/1768* (2015.01)

(58) Field of Classification Search
CPC .. G06F 7/08; G06F 7/06; B65G 43/08; B65G 47/82; B65G 47/69
See application file for complete search history.

(56) References Cited

U.S. PATENT DOCUMENTS

| | | | | |
|---|---|---|---|---|
| 5,597,995 A | * | 1/1997 | Williams | ............... G06F 19/328 235/375 |
| 6,304,797 B1 | | 10/2001 | Shusterman | |
| 8,231,749 B2 | * | 7/2012 | Dent | ...................... G06Q 50/24 156/64 |

(Continued)

*Primary Examiner* — Thomas Randazzo
(74) *Attorney, Agent, or Firm* — Standley Law Group LLP

(57) ABSTRACT

An automated method and system for a conveyor holding system for holding vials of a multi-vial order in a holding pattern until all vials of the order have been filled by an automatic pill counter. The system uses RFID information to divert vials off the conveyor into the conveyor holding loop if all vials of the multi-vial order have not been filled. The system is adapted to divert the vials of the multi-vial order out of the holding loop when all vials of the multi-vial order have been filled.

20 Claims, 3 Drawing Sheets

(56) References Cited

U.S. PATENT DOCUMENTS

| | | | |
|---|---|---|---|
| 9,394,107 B1 * | 7/2016 | Eller | B21B 41/00 |
| 9,457,967 B1 * | 10/2016 | Mahar | B65G 51/42 |
| 9,741,197 B2 | 8/2017 | Ghouri et al. | |
| 9,846,566 B1 * | 12/2017 | Kapadia | G06F 19/00 |
| 2007/0010910 A1 | 1/2007 | Pinney et al. | |
| 2008/0059228 A1 | 3/2008 | Bossi et al. | |
| 2008/0119958 A1 | 5/2008 | Bear et al. | |
| 2011/0133948 A1 | 6/2011 | Ervin | |
| 2017/0199981 A1 * | 7/2017 | Joplin | G06F 19/3475 |

* cited by examiner

PRESORTER HOLDING SYSTEM AND METHOD FOR AUTOMATED PRESCRIPTION FULFILLMENT

CROSS-REFERENCE TO RELATED APPLICATIONS

This application is a continuation of U.S. application Ser. No. 15/473,135, filed Mar. 29, 2017, the content of which is hereby incorporated by reference as if fully recited herein.

BACKGROUND

The present invention is directed to the field of automated dispensing systems, more particularly to the transport of objects such as pharmacy bottles/vials through an automated dispensing system. The present invention relates to an automated method and system for a conveyor holding system for holding vials of a multi-vial order in a holding pattern until all vials of the order have been filled by an automatic pill counter. The system uses RFID information to diverter vials of the conveyor into the conveyor holding loop if all vials of the multi-vial order have not been filled. The system is adapted to divert the vials of the multi-vial order out of the holding loop when all vials of the multi-vial order have been filled.

Many health benefit plan providers and retail pharmacies offer their clients the option of obtaining prescription drugs by mail. Mail order pharmacies ship prescription drugs to a client's home so the client is not required to visit a pharmacy to fill a prescription in person. For clients with chronic conditions or other health conditions that require maintenance drugs, a mail order prescription program is an attractive benefit because it is more convenient for the clients and typically less expensive than obtaining prescription drugs at a neighborhood pharmacy. Clients have the option of purchasing many widely-prescribed maintenance drugs, for example, in a 60-day or even a 90-day supply at a lower cost than a 30-day supply.

Most mail order pharmacies use automated systems and dispensing lines to process and ship a high volume of prescriptions on a daily basis. Each prescription medication is typically dispensed into a vial or other container labeled with data from an electronic order that identifies the patient, drug (e.g., by NDC), dosage, and quantity. Each medication is dispensed in its own vial and in many instances, multiple vials are combined into a single package and shipped to a single address for a client with one or more chronic conditions requiring multiple medications. The automated dispensing system, therefore, must be intelligent and capable of determining which vials should be combined into a single package. The system must also be capable of routing the vials through the system to their appropriate destinations. Sensors deployed at many locations along the system detect the prescription information on the bottles along with RFID tag information to intelligently route and divert the vials to the appropriate conveyor or destination. If the vial is to be combined with other vials (multi-vial order), the vials are sorted and grouped together, preferably towards the end of the dispensing line. The vials are ultimately routed to the final location for packaging and mailing to the consumer.

Automated dispensing lines typically comprise multiple sorting stations and therefore, require functionality to route and divert vials to the appropriate station. The process of routing and diverting vials for sorting and consolidation as well as other reasons can increase vial travel and processing time.

Depending upon how the technology is implemented and deployed within a mail order pharmacy, a substantial number of steps in the fulfillment process may be automated and the need for human intervention minimized. Transporting bottles through the automated dispensing lines in an efficient, timely, accurate, and consistent manner is crucial for filling the high volume of mail order prescriptions.

One technique for processing multi-prescription orders is to group the vials for the order and process them together so that all vials arrive for packaging and shipping as a group. Although "group processing" of vials is a logical approach to processing and packaging vials destined for a single address, it is not an efficient approach. Implementation of "group processing" on an automated dispensing line may require development of sophisticated algorithms for determining a reasonable or adequate route for the vials to travel as well as holding or reordering of other orders to permit the vials for a multi-prescription order to travel on the line as a group. The requirement for holding and reordering of orders increases vial processing time. In addition, processing of the vials in a group may require longer overall travel times for the vials as the vials are routed as a group and required to make unnecessary stops at stations other than the one station that has the appropriate medication for the vial.

A more efficient approach to processing of multi-prescription orders involves processing each vial of medication separately and then sorting and consolidating or regrouping them for packaging and shipping to a single address. Single vial processing is typically more efficient than group vial processing and reduces the overall travel and processing time for each vial. Single vial processing, however, requires the development of methods for tracking the vials during processing and eventually, sorting and consolidating them for packaging and shipping. The sorting/consolidation process typically involves diverting vials of a multi-prescription order to a sorting station where vials are held until all of the vials for an order have arrived. The vials are grouped at the station and then released for packaging.

Processing times for vials on an automated dispensing line are impacted by various routing and diverting techniques that are employed to facilitate single vial processing as well as multi-prescription order processing. There is a need for an improved pharmaceutical vial processing system and method that reduces processing delays attributable to routing and diverting techniques.

Within a typical pharmacy production facility, there are automatic processes for the counting and sorting of pill tablets. For example, orders for vials of particular pills are processed automatically through an integrated system of pill counters and conveyors for transporting the vials to the appropriate outbound conveyor location (e.g., or a sorter location). Typically, these facilities are configured with multiple outbound conveyor lanes to allow for higher vial production volumes.

However, with this type of arrangement, multiple vials assigned to one specific order might be distributed to different take away or outbound conveyors which presents problems with the desired goal of getting all of the vials to reach the same downstream order sorter location. When a vial assigned to an order does not reach the designated order sorter location at approximately the same time as the other vials in the same order, the release of that order will be delayed, slowing order throughput and diminishing overall productivity of the system.

The automated pharmacy system of the present invention uses a presorter vial holding station at predetermined locations in the pharmacy line to hold vials (e.g., in a conveyor holding loop) until they can be released so that all vials in an order can reach an end downstream destination (e.g., sorter location) at approximately the same time. For example, in the present system, a presorter vial conveyor holding system is placed after the automatic pill/tablet counters (ATC) for diverting vials in a holding loop until other vials in the order are processed or filled by the ATCs. The use of the presorter holding loop ensures that vials of the same order reach the downstream sorter location at approximately the same time.

SUMMARY OF THE GENERAL INVENTIVE CONCEPT

In one embodiment of the invention, the invention is comprised of: a first inbound conveyor lane for transporting vials to the bank of automatic pill counters; a first outbound conveyor lane for transporting vials from the bank of automatic pill counters after the vials are filled with pills; a conveyor holding loop adjacent to the first outbound conveyor lane for holding vials in a holding pattern; a first mechanical diverter for pushing vials off the first outbound conveyor lane onto the conveyor holding loop; a first RFID reader for sensing RFID information from RFID tags near the first mechanical diverter; a second mechanical diverter for pushing vials off the conveyor holding loop onto the first outbound conveyor lane; a second RFID reader for sensing RFID information from RFID tags near the second mechanical diverter;
a first control processing system, the control processing system programmed with instructions executing on the processing system for: 1) receiving RFID information from the first and second RFID readers; 2) sending a first control signal to the first mechanical diverter to push a first vial off the first outbound conveyor lane and onto the conveyor holding loop if the first vial is part of a first multi-vial order and if all vials of the first multi-vial order have not been filled by an automatic pill counter; 3) sending a second control signal to the second mechanical diverter to push the first vial off the conveyor holding loop and onto the first outbound lane when all of the vials of the first multi-vial order have been filled by an automatic pill counter.

The foregoing and other features and advantages of the present invention will be apparent from the following more detailed description of the particular embodiments, as illustrated in the accompanying drawings.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

The following detailed description of the exemplary embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

Figure 1:
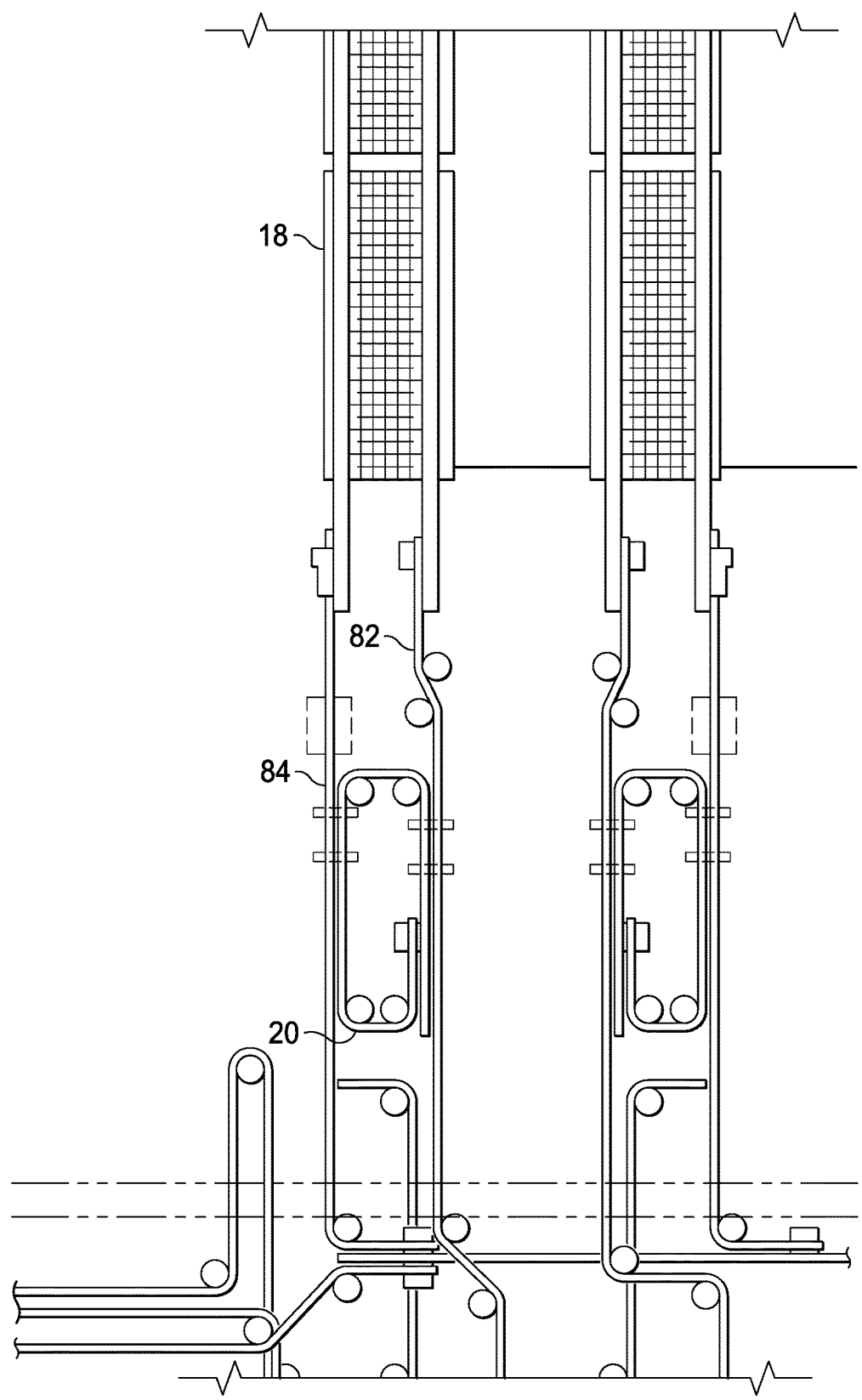
FIG. 1 illustrates an ATC bank.

Typically in an automated pharmacy system, once the vials leave labelers (e.g. prescription labels applied to the vials), they are transported via conveyors to a bank of automatic tablet counters (ATC). These ATC machines are lined up to form a row or lane. Each row of ATC machines is referred to as a "bank" of ATC machines. FIG. 1 illustrates a diagram of an ATC bank. The system is configured with multiple banks of ATC machines. Each of the ATC banks have an inbound lane 82 that transports vials into an ATC bank from the labelers and an outbound lane 84 for transporting vials out of the ATC bank once the vials have been filled with pills.

Each of the ATC machines store a particular type of pill or tablet for dispensing into vials as they move along the conveyor system. For example, one of the ATC machines might hold a large number of antibiotic pills in a canister. Once a vial reaches an ATC device, an RFID reader will read the RFID tag of the puck and the system will determine what type of pill or tablet the vial should receive. If the vial is to receive antibiotics, the vial will be diverted into the ATC lane for the ATC storing the antibiotic pills. The ATC will dispense the antibiotic pills into the vial and then release the vial to an outbound lane (e.g., at 84) for transport to the next step of the automated system—e.g., the capping stations where the vials are capped.

Figure 2A:
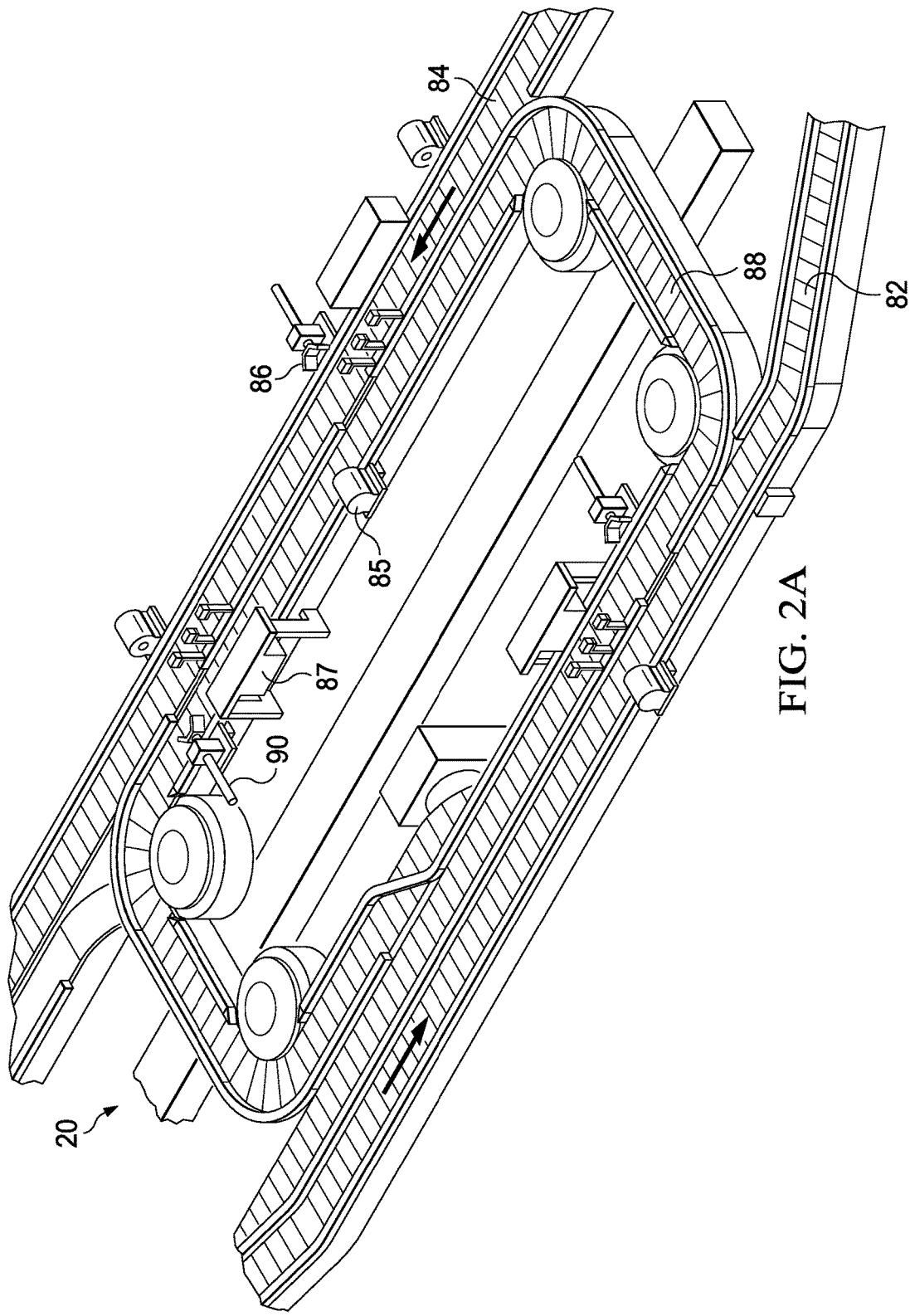
FIG. 2A illustrates one embodiment of the presorter vial conveyor holding system of the present invention.

Each of the outbound conveyor lanes leaving the ATC machines pass by a presorter vial conveyor holding system 20 located after the automatic pill/tablet counters 18 (ATC). The purpose of the presorter vial conveyor holding system is to hold vials in a holding pattern until other vials in the order are processed by the ATCs. FIG. 2A illustrates one embodiment of the presorter vial conveyor holding system of the present invention. The vials to be filled enter one of the 12 ATC banks via the inbound conveyor lane 82. After the vial is filled at one of the ATC machines, the puck/vial is released onto the outbound lane 84 for transport to the capping stations. (Each of the ATC banks have an inbound lane and an outbound lane). The filled vial will travel on the outbound lane past a presorter vial conveyor holding system 20. The vial will pass by a first RFID sensor/reader, shown generally at 85, that reads the RFID tag on the puck carrying the vial. The RFID is used by the control system to determine whether the vial is part of a multi-vial order and whether all of the vials of the order have been filled by one of the ATC machines. If the vial is part of a multi-vial order, and if there are vials of the order that have not been filled, the system diverts the vial into the presorter conveyor holding system by pushing the vial off the outbound lane using a diverter mechanism 86. In this embodiment, the diverter mechanism is a pneumatic powered mechanical arm that pushes the vial off the outbound lane into the presorter conveyor holding system.

Once in the presorter vial conveyor holding system, the vial will travel on a conveyor loop 88 until the control system determines that all of the vials of the multi-vial order have been filled by an ATC machine (in other words, the vials will be held in a holding pattern on the conveyor loop 88 until they are ready to be released back onto the outbound lane 84). In one embodiment, the control system will save information regarding each of the vials in a multi-vial order in a table stored in the system. For example, the table may have RFID information, prescription information, and whether the vial has been filled by an ATC machine. Once the control system determines that all of the vials of a particular multi-vial order have been filled by an ATC machine, the control system will then release all of the vials from the order that are in the presorter vial conveyor holding system. For example, another RFID reader/sensor, shown generally at 87, will sense an RFID tag of a vial/puck traveling on the conveyor loop, and if the control system determines that all of the vials of multi-vial order have been filled, a diverter mechanism 90 will push the vial back onto the outbound lane 84 to transport the vial to the next stage of the prescription fulfillment process.

Figure 2B:
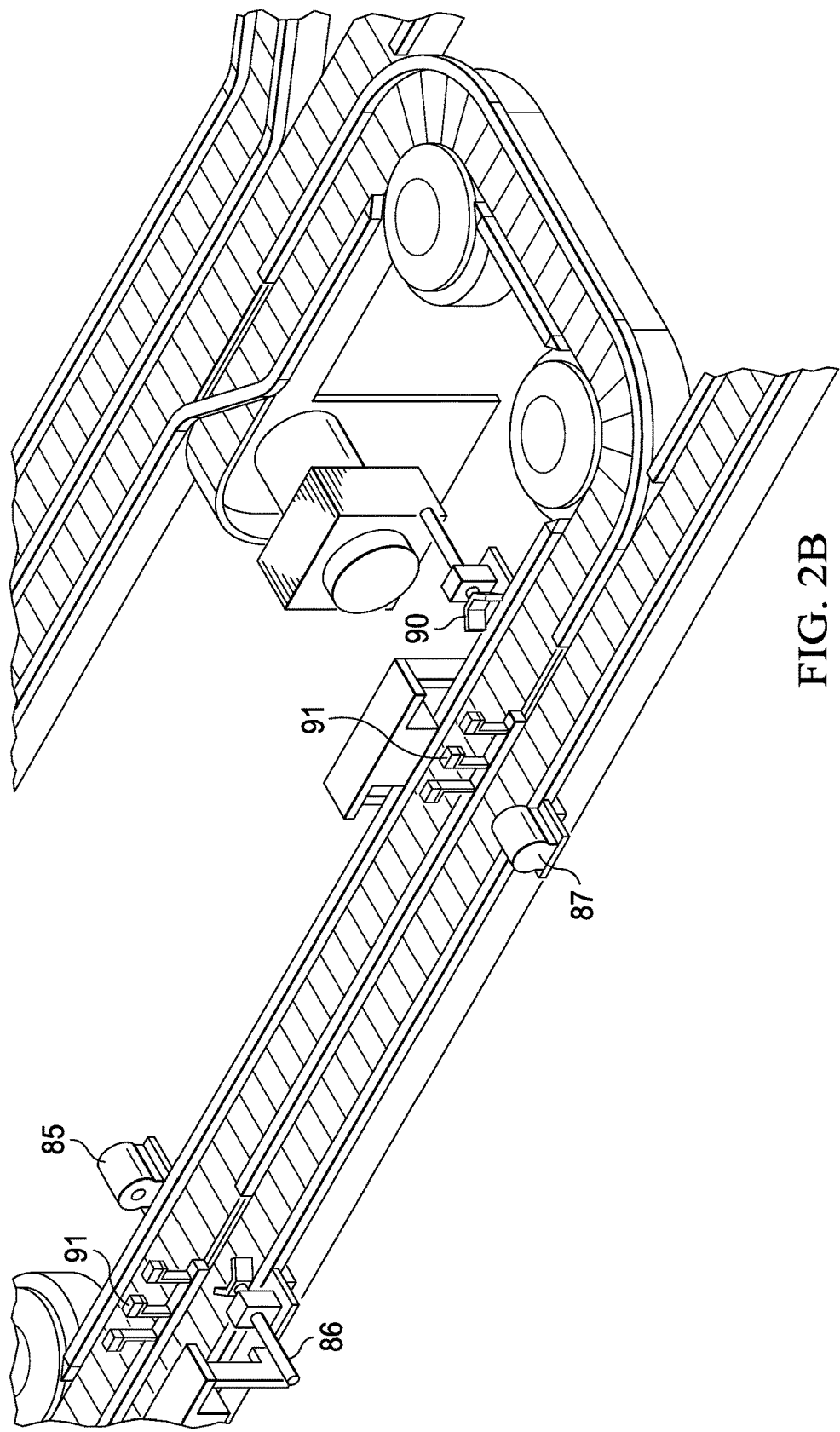
FIG. 2B illustrates a close-up view of the sensors and diverter mechanisms shown in FIG. 2A.

FIG. 2B illustrates a close-up view of the sensors and diverter mechanisms shown in FIG. 2A. As shown, each of the diverter mechanisms shown has a mechanical member at the end of the arm for pushing the vial off the conveyor and diverting it onto another conveyor. The mechanical member is preferably shaped in the form of a bracket or claw for catching the vial as it pushes the vial off the conveyor it is traveling on. There is an RFID reader underneath the photo eye sensors that notes the information in the nearby puck (via RFID tag) and sends that information to the control system software. The RFID reader sends puck RFID information while the photo-eye sensors 91 send location information, i.e., "a puck is here." This location information helps the system know when to actuate the mechanical diverts or hold-backs of the vial/pucks. The control system receives the information and issues a respective command to the actuators, which are the holdbacks and diverts. Photo eye sensors, or photoelectric sensors, detect objects using transmitted light (e.g., objects moving through the light).

This presorter vial conveyor holding system is used to maintain multiple-vial orders in close proximity together as they travel through the pharmacy line. This presorter "loop" is placed after the ATC machines and is configured with sensors to detect (via RF tags on the pucks, and photo eye sensors) prescription vials as they leave the ATC machines. If one of the vials in the order is delayed for some reason, the other vials in the order will be diverted into a presorter loop for holding purposes. For example, if one of the ATC drug canisters is empty, the vial cannot be filled until the canister is replenished. In this situation, because one of the vials of the multi-vial order cannot be filled, this will cause a delay in the order fulfillment for that order. Accordingly, if the system determines that one of the vials of a multi-vial order is delayed, all of the other vials of that order will be diverted into the presorter loop to be held until the last vial for that order is filled and released by an ATC. Once the last vial has been filled by an ATC, the system releases all the other vials being held in the presorter loop so that all of the vials of the order can proceed to the next stage of the prescription fulfillment system in close proximity to each other.

In other words, as vials that have been filled and released by an ATC machine approach the presorter loop, RFID readers determine if a vial is from a multi-vial order, and if so, checks to see if all of the vials of that order have been filled by one of the ATC machines. If not, a diversion mechanism, diverts the vial into the presorter loop for holding purposes (e.g., the vials travel in a conveyor loop until they are released back onto the conveyor system for transport to the next stage of the system). Once the last vial in the order is filled by the ATC machines, a control signal is sent to the presorter loop to release the vials of the order so all of the vials can proceed through the pharmacy line in close proximity to each other. This process enables the multiple vials from one order to reach the sorter stage of the pharmacy line in close proximity to one another so that all the vials can be combined together for packaging and mailing.

In one embodiment of the system, the system is adapted to divert vials from the conveyor holding loop to an exceptions processing station after a predetermined period of time. These vials are generally deemed to be part of an order that is missing vials. Thus, after vials are held in the conveyor holding loop for a certain period of time (e.g., 36.6 seconds), the control system (using the diverters previously discussed), diverts these vials out of the holding loop where they are then diverted to an exceptions stations where they are manually processed.

While certain embodiments of the present invention are described in detail above, the scope of the invention is not to be considered limited by such disclosure, and modifications are possible without departing from the spirit of the invention as evidenced by the following claims.

What is claimed is:

1. A vial conveyor holding system placed after a bank of automatic pill counters in an automatic prescription fulfillment system, the vial conveyor holding system comprising:
   a first conveyor lane for transporting vials after the vials are filled with pills;
   a conveyor holding loop adjacent to the first conveyor lane for holding vials in a holding pattern;
   a first mechanical diverter for pushing vials off the first conveyor lane onto the conveyor holding loop;
   a first RFID reader for sensing RFID information from RFID tags near the first mechanical diverter;
   a second mechanical diverter for pushing vials off the conveyor holding loop;
   a second RFID reader for sensing RFID information from RFID tags near the second mechanical diverter;
   a first control processing system, the control processing system programmed with instructions executing on the processing system for: 1) receiving RFID information from the first and second RFID readers; 2) sending a first control signal to the first mechanical diverter to push a first vial off the first conveyor lane and onto the conveyor holding loop if the first vial is part of a first multi-vial order and if all vials of the first multi-vial order have not been filled by an automatic pill counter; 3) sending a second control signal to the second mechanical diverter to push the first vial off the conveyor holding loop when all of the vials of the first multi-vial order have been filled by an automatic pill counter.

2. The vial conveyor holding system of claim 1, further comprising:
   a first photoelectric sensor placed near the first mechanical diverter for sensing the presence of vials passing by the first photoelectric sensor;
   a second photoelectric sensor placed near the second mechanical diverter for sensing the presence of vials passing by the second photoelectric sensor;
   wherein the control processing system is programmed with instructions executing on the processing system for: 1) receiving signals from the first and second photoelectric sensor; and 2) timing the sending of the first control signal to the first mechanical diverter to push the first vial onto the conveyor holding loop based on the signal received from the first photoelectric sensor; 3) timing the sending of the second control signal to the second mechanical diverter to push the first vial off the conveyor holding loop based on the signal received from the second photoelectric sensor.

3. The vial conveyor holding system of claim 1, wherein the first and second mechanical diverters are rods wherein each rod has a mechanical member for pushing vials.

4. The vial conveyor holding system of claim 1, wherein the first and second mechanical members are each comprised of a motor and a rotating member for pushing vials.

5. The vial conveyor holding system of claim 1, wherein the control processing system is programmed with instructions executing on the processing system for: 1) saving information regarding each of the vials in the first multi-vial order in a table stored in the system; and 2) saving in the table for each of the vials in the first multi-vial order, RFID information, prescription information, and information on whether the vial has been filled by an ATC machine.

6. The vial conveyor holding system of claim 1, wherein the system is adapted to divert vials from the conveyor holding loop to an exceptions processing station after a predetermined period of time.

7. The vial conveyor holding system of claim 1, wherein the conveyor holding loop is a conveyor adapted to move vials in a loop holding pattern.

8. The vial conveyor holding system of claim 7, wherein the loop is in an oval or circular shape.

9. A vial conveyor holding system placed after a bank of automatic pill counters in an automatic prescription fulfillment system, the vial conveyor holding system comprising:
a first conveyor lane for transporting vials after the vials are filled with pills;
a conveyor holding loop adjacent to the first conveyor lane for holding vials in a holding pattern;
a first mechanical diverter for pushing vials off the first conveyor lane onto the conveyor holding loop;
a first RFID reader for sensing RFID information from RFID tags near the first mechanical diverter;
a second mechanical diverter for pushing vials off the conveyor holding loop;
a second RFID reader for sensing RFID information from RFID tags near the second mechanical diverter;
a first photoelectric sensor placed near the first mechanical diverter for sensing the presence of vials passing by the first photoelectric sensor;
a second photoelectric sensor placed near the second mechanical diverter for sensing the presence of vials passing by the second photoelectric sensor;
a first control processing system, the control processing system programmed with instructions executing on the processing system for: 1) receiving RFID information from the first and second RFID readers; 2) sending a first control signal to the first mechanical diverter to push a first vial off the first conveyor lane and onto the conveyor holding loop if the first vial is part of a first multi-vial order and if all vials of the first multi-vial order have not been filled by an automatic pill counter; 3) sending a second control signal to the second mechanical diverter to push the first vial off the conveyor holding loop when all of the vials of the first multi-vial order have been filled by an automatic pill counter; 4) receiving signals from the first and second photoelectric sensor; and 5) timing the sending of the first control signal to the first mechanical diverter to push the first vial onto the conveyor holding loop based on the signal received from the first photoelectric sensor; and 6) timing the sending of the second control signal to the second mechanical diverter to push the first vial off the conveyor holding loop based on the signal received from the second photoelectric sensor.

10. The vial conveyor holding system of claim 9, wherein the first and second mechanical diverters are rods wherein each rod has a mechanical member for pushing vials.

11. The vial conveyor holding system of claim 9, wherein the first and second mechanical members are each comprised of a motor and a rotating member for pushing vials.

12. The vial conveyor holding system of claim 9, wherein the control processing system is programmed with instructions executing on the processing system for: 1) saving information regarding each of the vials in the first multi-vial order in a table stored in the system; and 2) saving in the table for each of the vials in the first multi-vial order, RFID information, prescription information, and information on whether the vial has been filled by an ATC machine.

13. The vial conveyor holding system of claim 9, wherein the conveyor holding loop is a conveyor adapted to move vials in a loop holding pattern.

14. The vial conveyor holding system of claim 13, wherein the loop is in an oval or circular shape.

15. A vial conveyor holding system placed after a bank of automatic pill counters in an automatic prescription fulfillment system, the vial conveyor holding system comprising:
a first conveyor lane for transporting vials from the bank of automatic pill counters after the vials are filled with pills;
a conveyor holding loop adjacent to the first conveyor lane for holding vials in a holding pattern;
a first mechanical diverter for pushing vials off the first conveyor lane onto the conveyor holding loop;
a first RFID reader for sensing RFID information from RFID tags near the first mechanical diverter;
a second mechanical diverter for pushing vials off the conveyor holding;
a second RFID reader for sensing RFID information from RFID tags near the second mechanical diverter;
a first control processing system, the control processing system programmed with instructions executing on the processing system for: 1) receiving RFID information from the first and second RFID readers; 2) saving information regarding each of the vials in a first multi-vial order in a table stored in the system; 3) saving in the table for each of the vials in the first multi-vial order, RFID information, prescription information, and information on whether the vial has been filled by an ATC machine; 4) sending a first control signal to the first mechanical diverter to push a first vial off the first conveyor lane and onto the conveyor holding loop if the first vial is part of the first multi-vial order and if all vials of the first multi-vial order have not been filled by an automatic pill counter; and 5) sending a second control signal to the second mechanical diverter to push the first vial off the conveyor holding loop when all of the vials of the first multi-vial order have been filled by an automatic pill counter.

16. The vial conveyor holding system of claim 15, further comprising:
a first photoelectric sensor placed near the first mechanical diverter for sensing the presence of vials passing by the first photoelectric sensor;
a second photoelectric sensor placed near the second mechanical diverter for sensing the presence of vials passing by the second photoelectric sensor;
wherein the control processing system is programmed with instructions executing on the processing system for: 1) receiving signals from the first and second photoelectric sensor; 2) timing the sending of the first control signal to the first mechanical diverter to push the first vial onto the conveyor holding loop based on the signal received from the first photoelectric sensor; and 3) timing the sending of the second control signal to the second mechanical diverter to push the first vial off the conveyor holding loop based on the signal received from the second photoelectric sensor.

17. The vial conveyor holding system of claim 15, wherein the first and second mechanical diverters are rods wherein each rod has a mechanical member for pushing vials.

18. The vial conveyor holding system of claim 15, wherein the first and second mechanical members are each comprised of a motor and a rotating member for pushing vials.

19. The vial conveyor holding system of claim 15, wherein the conveyor holding loop is a conveyor adapted to move vials in a loop holding pattern.

20. The vial conveyor holding system of claim 19, wherein the loop is in an oval or circular shape.

\* \* \* \* \*